United States Patent
Shepard et al.

(10) Patent No.: US 9,841,416 B2
(45) Date of Patent: Dec. 12, 2017

(54) SYSTEMS AND METHODS FOR SINGLE-MOLECULE NUCLEIC-ACID ASSAY PLATFORMS

(71) Applicant: The Trustees of Columbia University in the City of New York, New York, NY (US)

(72) Inventors: Kenneth L. Shepard, Ossining, NY (US); Steven Warren, White Plains, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/509,766

(22) Filed: Oct. 8, 2014

(65) Prior Publication Data

US 2015/0093849 A1   Apr. 2, 2015

Related U.S. Application Data

(63) Continuation of application No. PCT/US2013/031745, filed on Mar. 14, 2013.

(Continued)

(51) Int. Cl.
*G01N 33/53* (2006.01)
*B82Y 10/00* (2011.01)
(Continued)

(52) U.S. Cl.
CPC .... *G01N 33/5308* (2013.01); *B01L 3/502707* (2013.01); *B01L 7/52* (2013.01); *B82Y 10/00* (2013.01); *G01N 27/4145* (2013.01); *G01N 27/4146* (2013.01); *H01L 51/0002* (2013.01); *H01L 51/0048* (2013.01);
(Continued)

(58) Field of Classification Search
CPC ............................................ H01L 2924/12032
See application file for complete search history.

(56) References Cited

U.S. PATENT DOCUMENTS 5,304,950 A   4/1994  Martin et al.
5,599,668 A   2/1997  Stimpson et al.
(Continued)

FOREIGN PATENT DOCUMENTS

CN   101126735 A   2/2008
CN   101194162 A   6/2008
(Continued)

OTHER PUBLICATIONS

Label-free single-molecule detection of DNA hybridization kinetics with a carbon nanotube field-effect transistor, Published Jan. 23, 2011.*
(Continued)

*Primary Examiner* — Caridad Everhart
*Assistant Examiner* — Ankush Singal
(74) *Attorney, Agent, or Firm* — Baker Botts L.L.P.

(57) ABSTRACT

Integrated circuits for a single-molecule nucleic-acid assay platform, and methods for making such circuits are disclosed. In one example, a method includes transferring one or more carbon nanotubes to a complementary metal-oxide semiconductor (CMOS) substrate, and forming a pair of post-processed electrodes on the substrate proximate opposing ends of the one or more carbon nanotubes.

12 Claims, 18 Drawing Sheets

Related U.S. Application Data

(60) Provisional application No. 61/636,459, filed on Apr. 20, 2012, provisional application No. 61/680,094, filed on Aug. 6, 2012.

(51) Int. Cl.
| | | |
|---|---|---|
| *H01L 51/00* | (2006.01) | |
| *B01L 3/00* | (2006.01) | |
| *B01L 7/00* | (2006.01) | |
| *G01N 27/414* | (2006.01) | |
| *B82Y 15/00* | (2011.01) | |
| *H01L 23/00* | (2006.01) | |
| *B82Y 40/00* | (2011.01) | |
| *H01L 29/775* | (2006.01) | |
| *H01L 29/06* | (2006.01) | |
| *H01L 51/05* | (2006.01) | |

(52) U.S. Cl.
CPC . *H01L 51/0049* (2013.01); *B01J 2219/00653* (2013.01); *B01J 2219/00722* (2013.01); *B01L 2300/0645* (2013.01); *B01L 2300/0663* (2013.01); *B01L 2300/0887* (2013.01); *B01L 2300/0896* (2013.01); *B01L 2300/1827* (2013.01); *B82Y 15/00* (2013.01); *B82Y 40/00* (2013.01); *H01L 24/48* (2013.01); *H01L 29/0673* (2013.01); *H01L 29/775* (2013.01); *H01L 51/0558* (2013.01); *H01L 2224/45144* (2013.01); *H01L 2224/48227* (2013.01); *H01L 2924/00014* (2013.01); *H01L 2924/12032* (2013.01)

(56) References Cited

U.S. PATENT DOCUMENTS

| | | | |
|---|---|---|---|
| 6,030,115 A | 2/2000 | Ishiguro et al. | |
| 7,056,670 B2 | 6/2006 | Odedra | |
| 7,208,077 B1 | 4/2007 | Albers et al. | |
| 7,468,271 B2 | 12/2008 | Golovchenko et al. | |
| 7,491,628 B2 | 2/2009 | Noca et al. | |
| 7,635,423 B2 | 12/2009 | Boussaad et al. | |
| 7,666,593 B2 | 2/2010 | Lapidus | |
| 7,767,400 B2 | 8/2010 | Harris | |
| 7,790,391 B2 | 9/2010 | Harris et al. | |
| 7,948,015 B2 | 5/2011 | Rothberg et al. | |
| 8,013,366 B2 | 9/2011 | Lee et al. | |
| 8,038,943 B2 | 10/2011 | Yoo et al. | |
| 2002/0006357 A1 | 1/2002 | McGeoch et al. | |
| 2002/0022226 A1 | 2/2002 | Nakao et al. | |
| 2003/0087292 A1 | 5/2003 | Chen et al. | |
| 2004/0028875 A1* | 2/2004 | Van Rijn | A61L 27/50 428/98 |
| 2004/0055901 A1 | 3/2004 | Petersen et al. | |
| 2004/0238379 A1 | 12/2004 | Lindsay et al. | |
| 2005/0145496 A1 | 7/2005 | Goodsaid et al. | |
| 2005/0181383 A1 | 8/2005 | Su et al. | |
| 2005/0191495 A1 | 9/2005 | Rueckes et al. | |
| 2006/0078468 A1 | 4/2006 | Gabriel et al. | |
| 2006/0194263 A1 | 8/2006 | Boussad et al. | |
| 2006/0240543 A1 | 10/2006 | Folch et al. | |
| 2006/0246443 A1* | 11/2006 | Bockelmann | C12Q 1/6825 435/29 |
| 2006/0246497 A1* | 11/2006 | Huang | G01N 27/4146 435/6.14 |
| 2007/0292855 A1 | 12/2007 | Dubin et al. | |
| 2008/0035494 A1* | 2/2008 | Gomez | B82Y 15/00 205/792 |
| 2008/0094076 A1 | 4/2008 | Hibbs et al. | |
| 2008/0191718 A1* | 8/2008 | Wolkow | B82Y 10/00 324/691 |
| 2008/0203380 A1 | 8/2008 | Wang et al. | |
| 2008/0214494 A1* | 9/2008 | Mohapatra | A61K 48/0041 514/55 |
| 2008/0274912 A1* | 11/2008 | Johnson | B82Y 30/00 506/13 |
| 2009/0026082 A1 | 1/2009 | Rothberg et al. | |
| 2009/0142504 A1 | 6/2009 | Ervin et al. | |
| 2009/0173527 A1 | 7/2009 | Benke et al. | |
| 2009/0181381 A1 | 7/2009 | Oldham et al. | |
| 2009/0305319 A1 | 12/2009 | Baudenbacher et al. | |
| 2009/0325350 A1 | 12/2009 | Radosavljevic et al. | |
| 2010/0088040 A1* | 4/2010 | Johnson, Jr. | C12Q 1/6825 702/27 |
| 2010/0148126 A1 | 6/2010 | Guan et al. | |
| 2010/0285637 A1 | 11/2010 | Khan et al. | |
| 2010/0327874 A1 | 12/2010 | Liu et al. | |
| 2010/0331194 A1 | 12/2010 | Turner et al. | |
| 2011/0057725 A1 | 3/2011 | Ikeda et al. | |
| 2011/0101996 A1 | 5/2011 | Potyrailo et al. | |
| 2011/0105870 A1 | 5/2011 | Dale et al. | |
| 2011/0147714 A1* | 6/2011 | Hong | B82Y 10/00 257/24 |
| 2011/0220775 A1 | 9/2011 | Triener et al. | |
| 2011/0263463 A1 | 10/2011 | Rothberg et al. | |
| 2012/0025414 A1 | 2/2012 | Schmidt et al. | |
| 2012/0061239 A1 | 3/2012 | Elibol et al. | |
| 2012/0064519 A1 | 3/2012 | Fang et al. | |
| 2012/0234679 A1* | 9/2012 | Garaj | B82Y 30/00 204/520 |
| 2013/0180867 A1 | 7/2013 | Rosenstein et al. | |
| 2013/0224879 A1 | 8/2013 | Shepard et al. | |
| 2013/0285680 A1 | 10/2013 | Sorgenfrei et al. | |
| 2014/0048416 A1 | 2/2014 | Rosenstein et al. | |
| 2015/0090588 A1 | 4/2015 | Shepard et al. | |
| 2015/0369776 A1 | 12/2015 | Rosenstein et al. | |

FOREIGN PATENT DOCUMENTS

| | | |
|---|---|---|
| CN | 101346472 A | 1/2009 |
| WO | WO 2006/024023 | 3/2006 |
| WO | WO 2007/075967 A2 | 7/2007 |
| WO | WO 2008/132643 | 11/2008 |
| WO | WO 2009/046110 | 4/2009 |
| WO | WO 2010/030057 | 3/2010 |
| WO | WO 2011/123525 | 10/2011 |
| WO | WO 2012/021149 | 2/2012 |
| WO | WO 2012/042226 | 4/2012 |
| WO | WO 2012/044857 | 4/2012 |

OTHER PUBLICATIONS

U.S. Appl. No. 13/787,341, Jun. 12, 2015 Notice of Allowance.
U.S. Appl. No. 13/787,341, Apr. 14, 2015 Response to Non-Final Office Action.
U.S. Appl. No. 13/787,341, Jan. 15, 2015 Non-Final Office Action.
U.S. Appl. No. 13/942,242, Jan. 22, 2015 Non-Final Office Action.
U.S. Appl. No. 13/595,106, Jun. 24, 2015 Notice of Allowance.
U.S. Appl. No. 13/595,106, Dec. 18, 2014 Amendment and Request for Continued Examination (RCE).
U.S. Appl. No. 13/595,106, Dec. 18, 2014 Response after Final Office Action.
U.S. Appl. No. 13/595,106, Oct. 6, 2014 Applicant Initiated Interview Summary.
U.S. Appl. No. 13/595,106, Jun. 25, 2014 Final Office Action.
U.S. Appl. No. 13/595,106, May 5, 2014 Response to Non-Final Office Action.
U.S. Appl. No. 13/595,106, Apr. 25, 2014 Applicant Initiated Interview Summary.
U.S. Appl. No. 13/595,106, Feb. 5, 2014 Non-Final Office Action.
Anderson, et al., "A Label-free CMOS DNA Microarray based on Charge Sensing", Instrumentation and Measurement Technology Conference Proceedings, May 12-15, 2008, pp. 1631-1636.
Arata, et al., "Millisecond Analysis of Double Stranded DNA with Flourescent Intercalator by Micro-Thermocontrol-Device", *Talanta*, 79(3):963-966 (2009).
Barilero, et al., "Fluorescent thermometers for dual-emission wavelength measurements: Molecular engineering and application to thermal imaging in a microsystem" *Analytical Chemistry*, 2009, 81(19): 7988-8000.

(56) References Cited

OTHER PUBLICATIONS

Barilero, et al., *Analytical Chemistry*, 2009, 81: supplemental information.
Besteman, K. et al., "Enzyme-coated carbon nanotubes as single molecule biosensors", *Nano Letters, American Chemical Society*, vol. 3, No. 6, Jan. 5, 2003, pp. 727-730, XP002982648.
Office Action dated Nov. 19, 2014 in CN Patent Application No. 201280004265.8.
Extended EP Search Report dated Dec. 15, 2014 in EP Application No. 12734088.
Fu et al., "Label-free electrical detection of DNA hybridization using carbon nanotubes and graphene", *Nano Reviews*, vol. 1, No. 0, Aug. 31, 2010, XP055158479.
Goldsmith, et al., "Monitoring Single-Molecule Reactivity on a Carbon Nanotube", *Nano Letters*, 2008. 8(1): p. 189-194.
Goldsmith, et al., "Conductance-Controlled Point Functionalization of Single-Walled Carbon Nanotubes", *Science*, 2007. 315(5808): p. 77-81.
Gudnason, et al., "Comparison of Multiple DNA Dyes for Real-Time PCR: Effects of Dye Concentration and Sequence Composition on DNA Amplification and Melting Temperature", *Nucleic Acids Reasearch*, 35(19):e127 (2007).
Hazani et al., "Confocal Fluorescence Imaging of DNA-Functionalized Carbon Nanotubes", *Nano Letters*, vol. 3, No. 2, Feb. 1, 2003, pp. 153-155, XP055157827.
Heller, et al., "Identifying the mechanism of biosensing with carbon nanotube transistors", *Nano Letters*, 2008. 8(2): p. 591-5.
Huang, et al., "Gene expression analysis with an integrated CMOS microarray by time-resolved fluorescence detection", *Biosensors and Bioelectronics*, vol. 26, pp. 2660-2665.
Kang, et al., "High-performance electronics using dense, perfectly aligned arrays of single-walled carbon nanotubes", *Nat Nano*, 2007. 2(4): p. 230-236.
Kim, et al., "Nanopore sensor for fast label-free detection of short double-stranded DNAs", *Biosensors and Bioelectronics*, vol. 22, Issue 12, pp. 2926-2931.
Levine, et al., "Real-time, multiplexed electrochemical DNA detection using an active complementary metal-oxide-semiconductor biosensor array with integrated sensor electronics", *Biosensors and Bioelectronics*, vol. 24, No. 7, pp. 1995-2001.
Meric, et al., "Hybrid carbon nanotube-silicon complementary metal oxide semiconductor circuits", *Journal of Vacuum Science & Technology B*, 2007. 25(6): p. 2577-2580.
Mortazavi, et al., "Mapping and quantifying mammalian transcriptomes by RNA-Seq.", *Nature Methods*, 2008. 5(7): p. 621-628.
Polk, et al., "Ag/AgCl microelectrodes with improved stability for microfluidics", *Sensors & Actuators: B. Chemical*, 2006. 114: p. 239-247.
Rosenblatt, et al., High performance electrolyte gated carbon nanotube transistors. Nano Letters, 2002. 2(8): p. 869-872.
Rosenstein, et al., "Integrated nanopore sensing platform with sub-microsecond temporal resolution", Nature Methods, Mar. 3, 2012.
So, et al., "Single-Walled Carbon Nanotube Biosensors Using Aptamers as Molecular Recognition Elements", *Journal of the American Chemical Society*, vol. 127, No. 34, Aug. 1, 2005, pp. 11906-11907, XP55032046.
Sorgenfrei et al., "Label-free single-molecule detection of DNA-hybridization kinetics with a carbon nanotube field-effect transistor", *Nature Nanotechnology*, vol. 6, No. 2, Jan. 23, 2011, pp. 126-132, XP055157740.
Sorgenfrei, et al., "Single-molecule electronic detection using nanoscale field-effect devices", Design Automation Conference (DAC), Jun. 5-9, 2011.
Sorgenfrei, et al., "Debye Screening in Single-Molecule Carbon Nanotube Field-Effect Sensors", *Nano Letters*, 2011. 11(9): p. 3739-3743.
Star, et al., "Label-free detection of DNA hybridization using carbon nanotube network field-effect transistors", Proceedings of the National Academy of Sciences, vol. 103, No. 4, Jan. 24, 2006, pp. 921-926, XP003023787.
Suzuki, et al., "Microtechnologies for membrane protein studies", *Anal Bioanal Chem.*, 391(8):2695-2702 (2008).
Tashiro, et al., "A Nanothermometer Based on the Different pi Stacking of B- and Z-DNA", *Angewandte Chemie International Edition*, 42(18):6018-6020 (2003).
Tashiro, et al., "The Molecular-Thermometer Based on B-Z-Transition of DNA", Nucleic Acids Symposium Series, 48(1):89-90 (2004).
Wanunu, et al., "Electrostatic focusing of unlabelled DNA into nanoscale pores using a salt gradient", *Nat Nano*, 2010. 5(2): p. 160-165.
Yin, et al. (IEEE, 2007).
Zhao, et al., "Stochastic sensing of biomolecules in a nanopore sensor array", *Nanotechnology*, vol. 19, No. 50, pp. 505504.
International Search Report and Written Opinion for PCT/US2013/031757, dated Jun. 4, 2013.
International Search Report and Written Opinion for PCT/US2013/031745, dated Jun. 4, 2013.
International Search Report and Written Opinion for PCT/US2012/026292, dated May 29, 2012.
International Search Report and Written opinion for PCT/US2012/020955, dated May 16, 2012.
U.S. Appl. No. 13/787,341, Nov. 16, 2015 Issue Fee Payment.
U.S. Appl. No. 13/787,341, Aug. 20, 2015 Notice of Allowance.
U.S. Appl. No. 13/787,341, Aug. 12, 2015 Request for Continued Examination (RCE).
U.S. Appl. No. 13/801,834, Apr. 20, 2016 Non-Final Office Action.
U.S. Appl. No. 13/801,834, Jan. 27, 2016 Response to Non-Final Office Action.
U.S. Appl. No. 13/801,834, Jul. 28, 2015 Non-Final Office Action.
U.S. Appl. No. 13/942,242, Jul. 30, 2015 Notice of Abandonment.
U.S. Appl. No. 13/595,106, Sep. 24, 2015 Issue Fee Payment.
U.S. Appl. No. 13/595,106, Dec. 9, 2013 Response to Restriction Requirement.
U.S. Appl. No. 13/595,106, Jul. 25, 2013 Restriction Requirement Filed.
Feldman et al., "Molecular Electronic Devices Based on Single-Walled Carbon Nanotube Electrodes," Accounts of Chemical Chemical Research 41(12):1731-1741 (Dec. 2008).
Guo et al., "Functional single-molecule devices based on SWNTs as point contacts," Journal of Materials Chemistry 19:5470-5473 (2009).
Liu et al., "Translocation of Single-Stranded DNA Through Single-Walled Carbon Nanotubes," Science 327(5961):64-67 (2010).
Yin et al., "A Low-Noise Preamplifier with Adjustable Gain and Bandwidth for Biopotential Recording Applications", IEEE, 2007, pp. 321-324.

\* cited by examiner

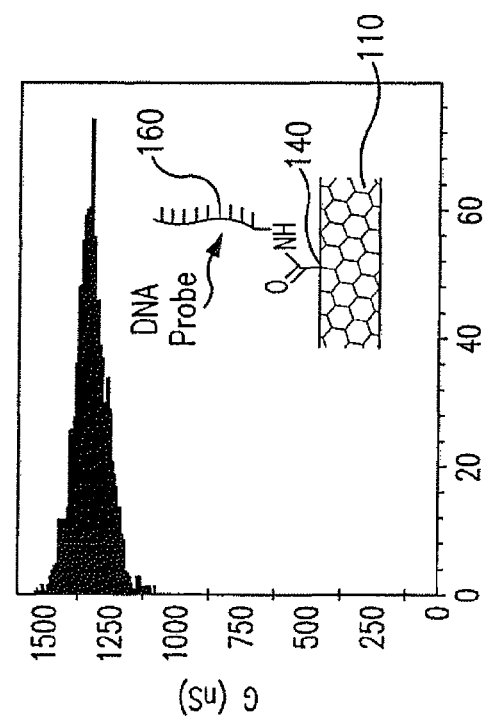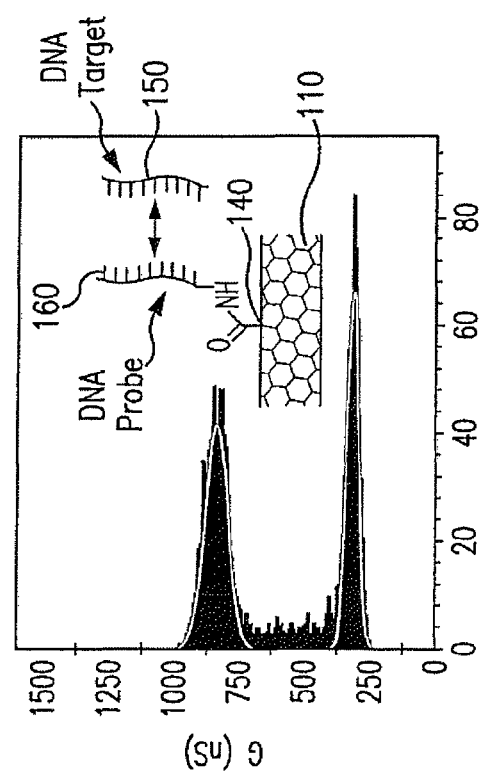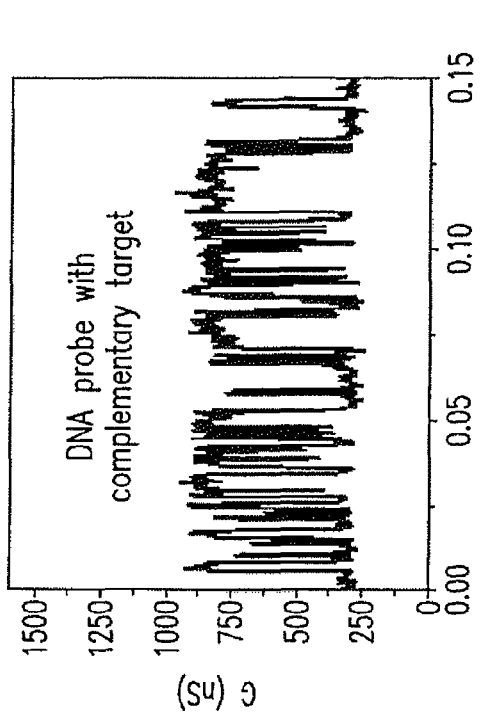

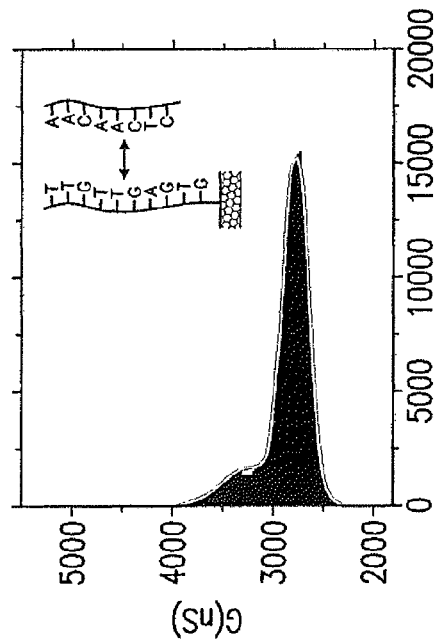
FIG. 4A
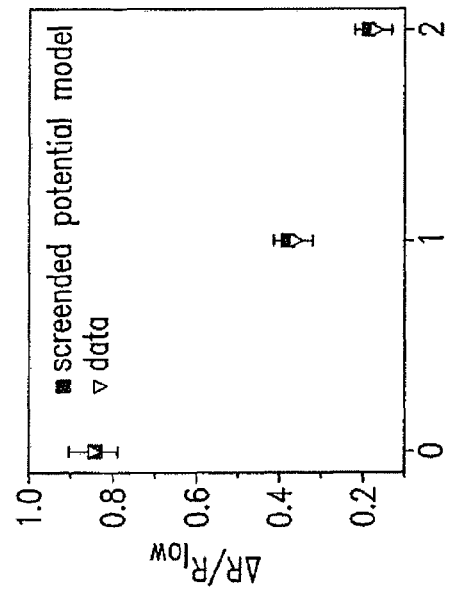
FIG. 4C
FIG. 4B
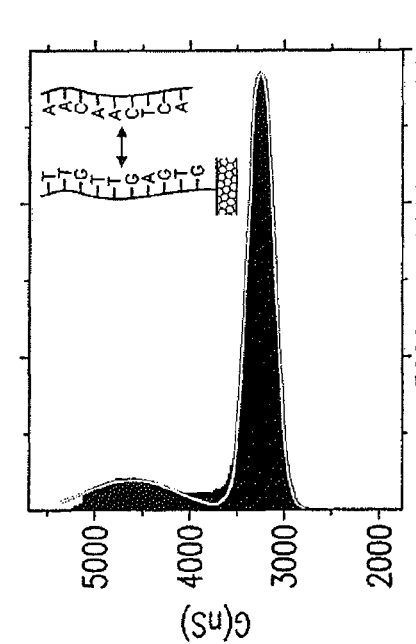
FIG. 4D

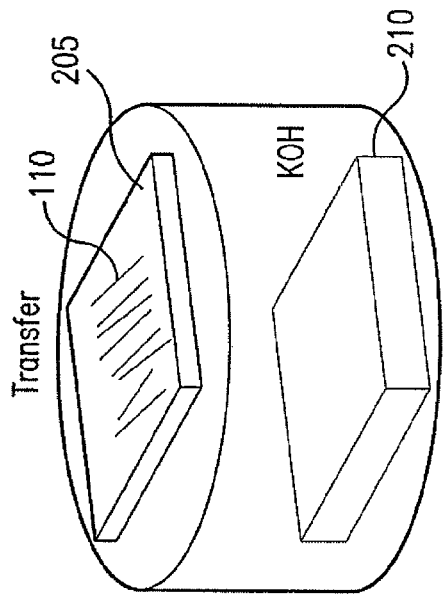
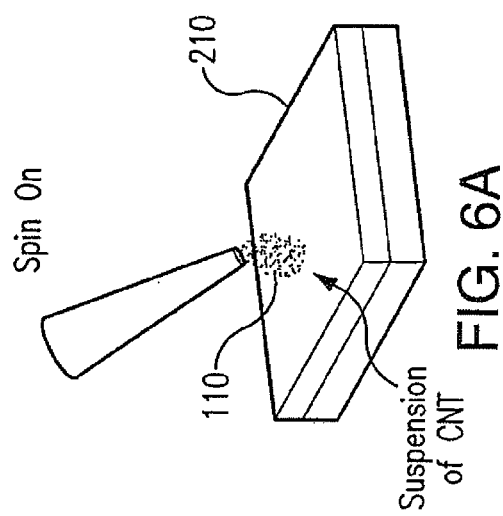
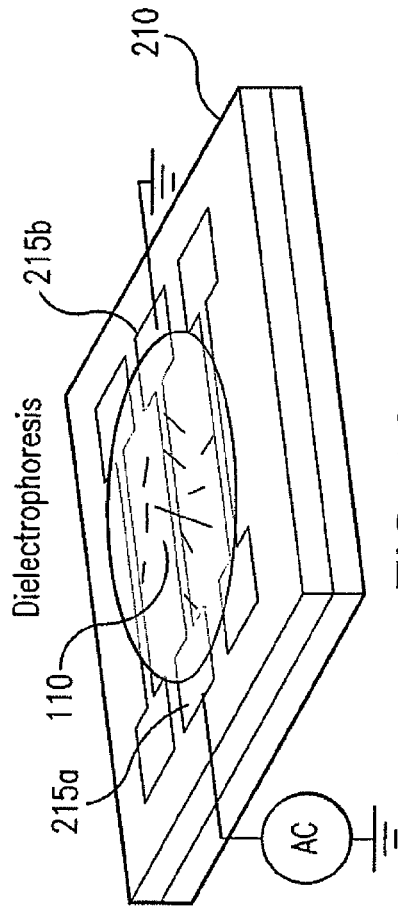
FIG. 6B
FIG. 6A
FIG. 6C

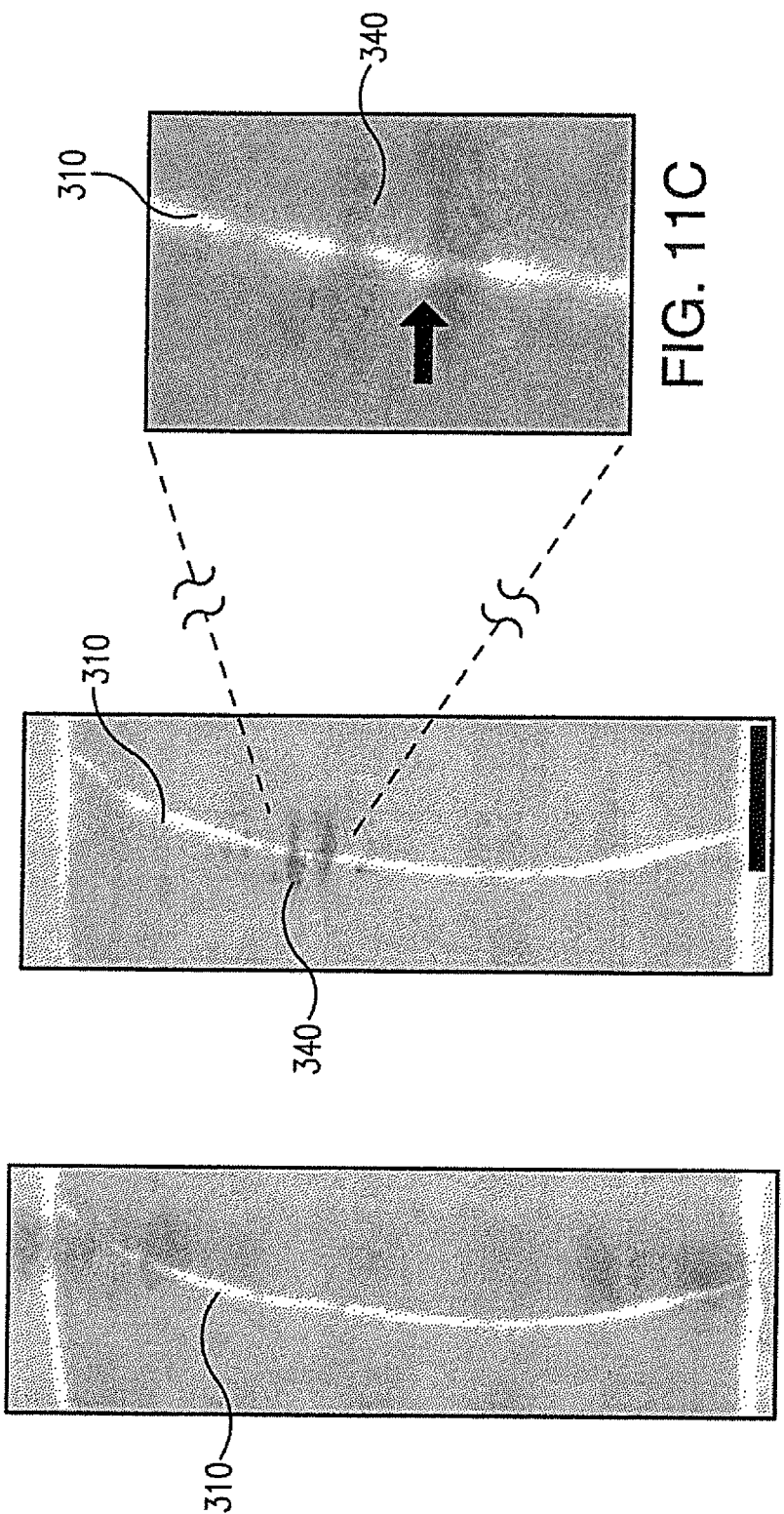

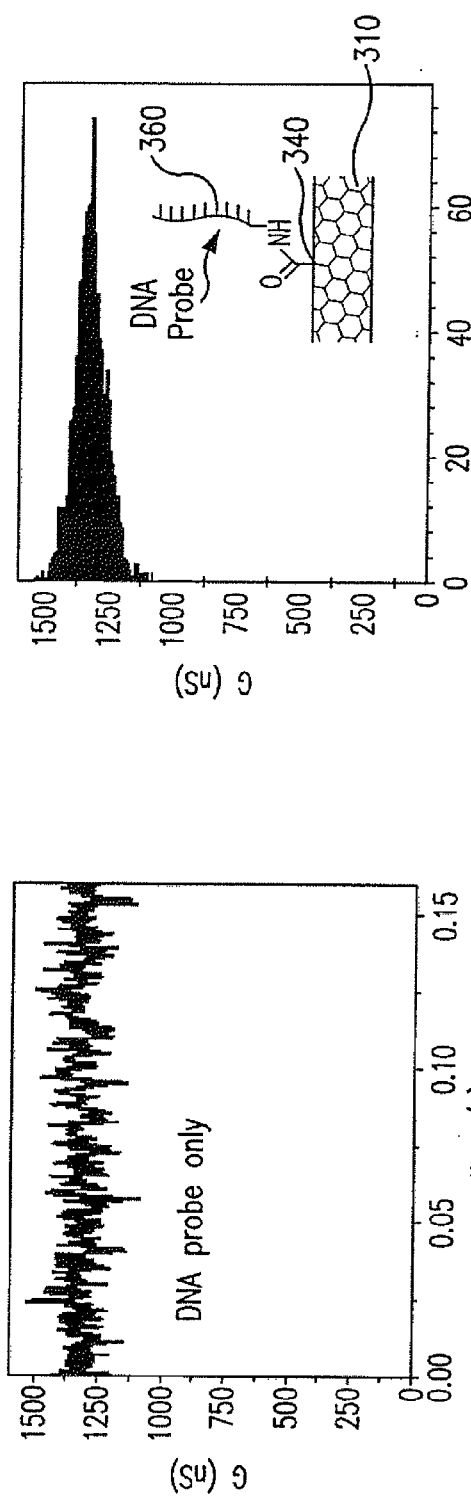
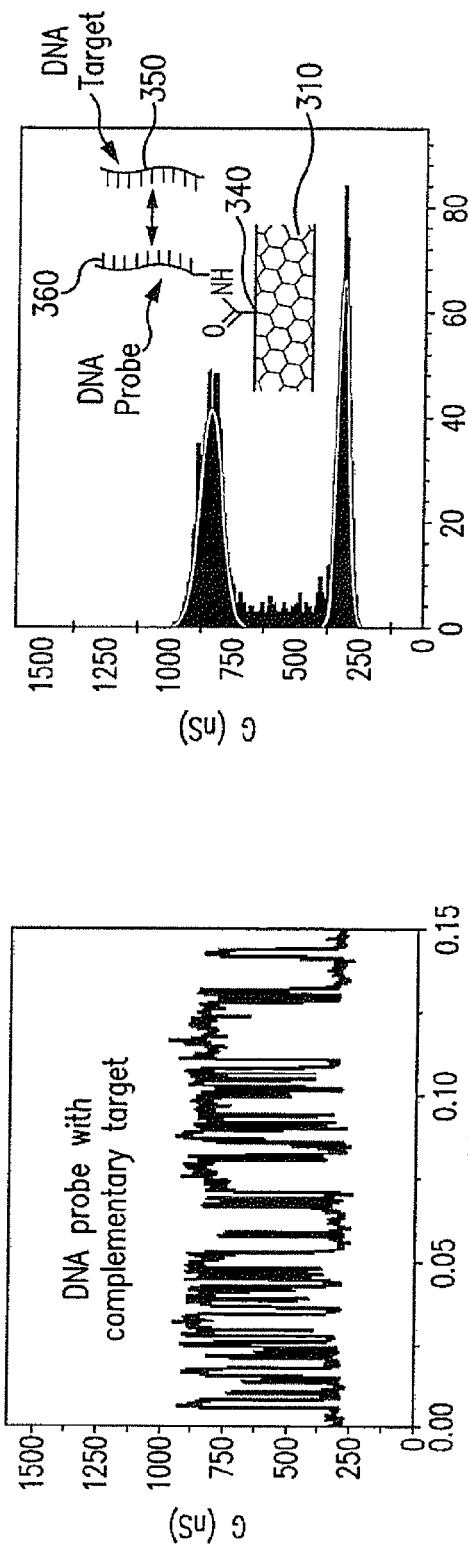

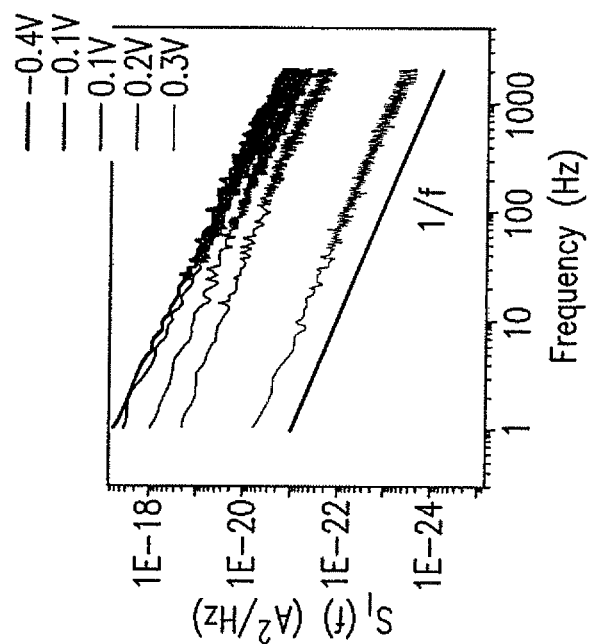
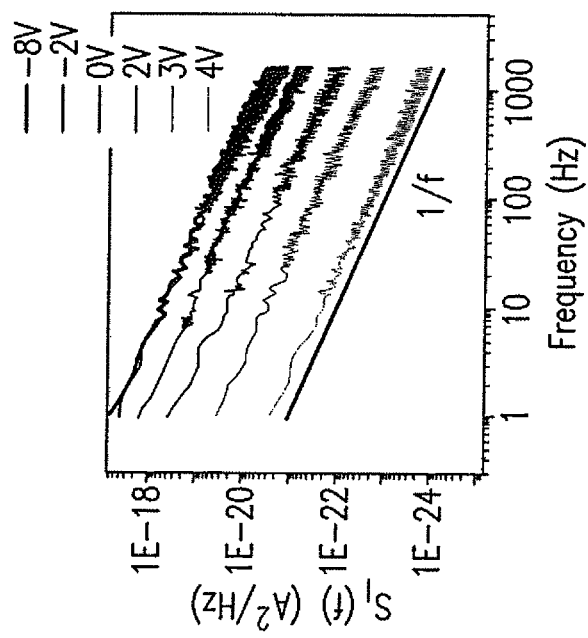

SEQUENCE LISTING

<160> NUMBER OF SEQ ID NOS: 4

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtgagttgtt                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aacaactcac                                                          10

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 aacaactc                                                            8

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 aacaactca                                                           9

SYSTEMS AND METHODS FOR SINGLE-MOLECULE NUCLEIC-ACID ASSAY PLATFORMS

CROSS-REFERENCE TO RELATED APPLICATIONS

This application is a continuation of PCT/US13/031745, filed Mar. 14, 2013 and which claims priority to U.S. Provisional Patent Application Ser. Nos. 61/636,459, filed on Apr. 20, 2012, and 61/680,094, filed on Aug. 6, 2012, each of which is incorporated by reference herein in its entirety.

GRANT INFORMATION

This invention was made with government support under grant 0707748 awarded by the National Science Foundation, and grants HG006879 and HG006882 awarded by the National Institute of Health. The government has certain rights in the invention.

SEQUENCE LISTING

This application contains a Sequence Listing, which has been submitted electronically in ASCII format and is hereby incorporated by reference in its entirety. Said ASCII copy, created on Oct. 29, 2014, is named 070050_5387_SL.txt and is 1,344 bytes in size.

BACKGROUND

The disclosed subject matter relates to single-molecule nucleic-acid assay platforms, including techniques for making integrated circuits for single-molecule nucleic-acid assay platforms.

Nucleic acid assays can have many applications, including, but not limited to, gene expression studies, environmental monitoring, and infectious disease recognition. Furthermore, polymerase chain reaction (PCR) can facilitate detection and quantitation of products. However, PCR can be challenging to implement in multiplexed analyses, at least in part because primer interactions can reduce sensitivity and the repertoire of reporter systems can allow for up to 10 to 20 targets. Sample preparation can include, for example, multiple stages of thermal cycling and precise control of enzymatic conditions.

In contrast, DNA microarray technology can allow for extensive multiplexing, but sensitivities can be too low to allow detection without amplification. As such, DNA microarray technology can also present the similar sample preparation complexities to PCR. With direct sequencing approaches, DNA can be directly sequenced for identification, but sensitivities can be too low to allow detection without amplification, and such techniques can be unsuitable for point-of-care diagnostics.

Accordingly, there remains an opportunity for single-molecule nucleic-acid assay platforms that can provide improved levels of sensitivity without amplification, while also providing improved multiplexing capabilities.

SUMMARY

Systems and methods for single-molecule nucleic-acid assay platforms, including techniques for making integrated circuits for single-molecule nucleic-acid assay platforms, are disclosed herein.

According to one aspect of the disclosed subject matter, methods of making an integrated circuit for a single-molecule nucleic-acid assay are provided. In one example, a method of making an integrated circuit for a single-molecule nucleic-acid assay platform includes transferring one or more carbon nanotubes to a complementary metal-oxide semiconductor (CMOS) substrate, and forming a pair of post-processed electrodes on the substrate proximate opposing ends of the one or more carbon nanotubes.

In some embodiments, transferring the one or more carbon nanotubes can include spinning the one or more carbon nanotubes from a suspension to the substrate. Additionally or alternatively, transferring the one or more carbon nanotubes can include forming the one or more carbon nanotubes on a transfer substrate, applying a layer of polymer to the transfer substrate to adhere the one or more carbon nanotubes to the transfer substrate, and placing the layer of polymer with the one or more carbon nanotubes on the CMOS substrate. Additionally or alternatively, transferring the one or more carbon nanotubes can include placing the one or more carbon nanotubes in a suspension proximate a pair of preformed electrodes on the substrate, and applying a voltage across the pair of preformed electrodes, so that a force is applied to the one or more carbon nanotubes to urge the carbon nanotubes to be disposed across the pair of preformed electrodes.

In some embodiments, the substrate can include surface-exposed electrodes. Forming the pair of post-processed electrodes can include depositing titanium on a pair of the surface-exposed electrodes. Additionally or alternatively, forming the pair of post-processed electrodes can include etching away a pair of surface-exposed electrodes and replacing the pair of surface-exposed electrodes with a pair of titanium electrodes.

The method can further include forming one or more reference electrodes on the substrate to allow control of an electrolytic gating potential. The substrate can include one or more surface-exposed electrodes, and forming the one or more reference electrodes can include etching away the surface-exposed electrodes. The one or more surface-exposed electrodes can include aluminum, and forming the one or more reference electrodes can further include replacing the surface-exposed electrodes with gold electrodes. Forming the one or more reference electrodes can further include electroplating silver on the gold electrodes. Forming the one or more reference electrodes can further include exposing the electroplated electrodes to FeCl3 to form Ag/AgCl electrodes. Additionally or alternatively, forming the one or more reference electrodes can include depositing platinum on the one or more surface-exposed electrodes. Additionally or alternatively, forming the one or more reference electrodes can include replacing the surface-exposed electrodes with one or more platinum electrodes.

In some embodiments, the method can further include forming a point defect on a portion of the one or more carbon nanotubes. The method can further include coupling the one or more post-processed electrodes to a ball-grid array (BGA) package. In some embodiments, the coupling can include wirebonding. Wirebonds can be exposed on the surface of the substrate, and the method can further include covering the exposed wirebonds using dam-and-fill material.

According to another aspect of the disclosed subject matter, integrated circuits for a single-molecule nucleic-acid assay platform are provided. In one example, integrated circuits for a single-molecule nucleic-acid assay platform can include a CMOS substrate and an array of single-molecule field-effect transistors (smFETs) disposed on a surface of the substrate. Each smFET can include one or more carbon nanotubes and a capture probe configured to provide target specificity for a single target nucleic acid molecule proximate thereto. The integrated circuit also includes at least one pair of electrodes disposed proximate opposing ends of the one or more carbon nanotubes to electrically couple the one or more carbon nanotubes to the substrate.

In some embodiments, the carbon nanotube can include a point defect formed on a portion thereof. The point defect can be configured to transmit the hybridization information for the single target nucleic acid molecule.

In some embodiments, the CMOS substrate can have dimensions of no more than 5 mm by 5 mm. The array can include at least 12 measurement channels. Each of the measurement channels can be multiplexed to at least 500 smFETs.

In some embodiments, the at least one pair of electrodes can include titanium. The integrated circuit can further include one or more reference electrodes to allow control of an electrolytic gating potential. The one or more reference electrodes can include one or more Ag/AgCl electrodes or platinum electrodes. The integrated circuit can include a ball-grid array (BOA) package coupled to the at least one pair of electrodes. The integrated circuit can further include a processor coupled to the array and configured to determine a capture rate from the hybridization information.

BRIEF DESCRIPTION OF THE DRAWINGS

FIGS. 3A-3D are diagrams illustrating further details of the assay platform of FIG. 1.

FIGS. 4A-4D are diagrams illustrating further details of the assay platform of FIG. 1. FIG. 4A-4C include illustrations of SEQ ID NOS 1-2, 1, 3, 1, and 4, respectively, in order of appearance.

FIGS. 6A-6C are diagrams illustrating exemplary techniques for transferring nanotubes onto an integrated circuit substrate.

FIGS. 11A-11C are diagrams illustrating further details of the assay platform of FIG. 8A.

FIGS. 12A-12D are diagrams illustrating further details of the assay platform of FIG. 8A.

FIGS. 15A-15D are diagrams illustrating further details of the assay platform of FIG. 8A.

DETAILED DESCRIPTION

The disclosed subject matter provides systems and methods for single-molecule nucleic-acid assay platforms. Single-molecule nucleic-acid assay platforms according to the disclosed subject matter can provide improved sensitivity without amplification, while also providing improved multiplexing capabilities. Transduction can be performed label-free, which can simplify sample preparation protocols.

Figure 1:
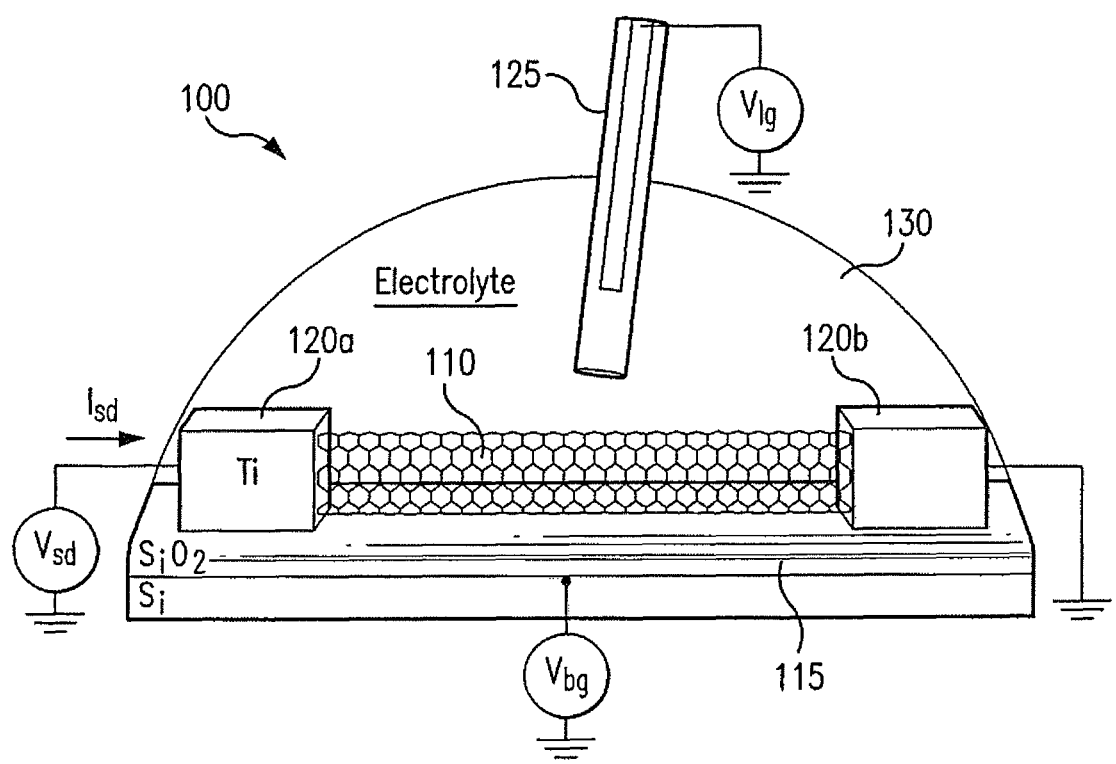
FIG. 1 is a diagram illustrating an exemplary embodiment of an assay platform according to the disclosed subject matter.

FIG. 1 is a diagram illustrating an exemplary nanoscale single-molecule field effect transistor (smFET) 100 according to the disclosed subject matter. A smFET 100, which can be utilized to perform transduction, can be configured as a carbon nanotube device 110 disposed on a substrate 115, which can be a silicon substrate and can have a silicon oxide layer disposed thereon. A capture probe 160 (as shown in FIGS. 3B and 3D), for example and as embodied herein single-stranded DNA, can be immobilized onto the nanotube 110, and can be coupled to source electrode 120a and drain electrode 120b, each of which are embodied herein as titanium electrodes, and can be disposed at opposing ends of the nanotube 110. To form source and drain electrodes 120a, 120b, a metal, such as titanium, can be deposited onto the substrate 120. Additionally, source and drain electrodes 120a, 120b can be passivated with a photoresist or an e-beam resist. The smFET 100 can be configured to detect hybridization with a single target molecule at a relatively high signal-to-noise ratio, for example 3 or more, without labeling. As such, background or non-specific adsorption can be reduced.

Figure 2:
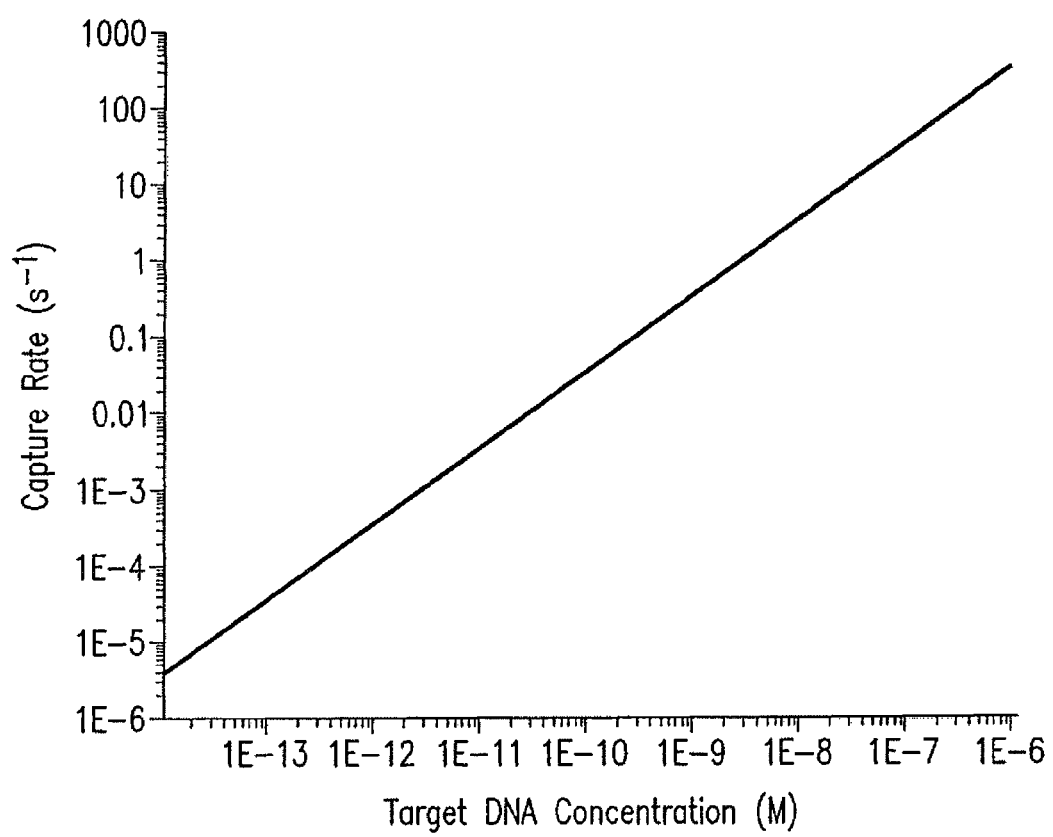
FIG. 2 is a diagram illustrating further details of the assay platform of FIG. 1.

The smFET 100 assay platform can operate differently from traditional ensemble assays. For example, and as embodied herein, rather than measuring the hybridization behavior of an ensemble, as in a traditional microarrays, the smFET 100 assay platform can measure the time between capture events. Capture rates can thus be diffusion limited and concentration dependent. As such, low levels of detection, as low as one molecule, can be performed, which can be affected at least in part by diffusion time of the target to the sensor site. With reference to FIG. 1, the diffusion time can be reduced with a bias applied between the nanotube 110 and a reference electrode 125, for example and embodied herein as an Ag/AgCl electrode or platinum electrode, in the electrolyte 130 that surrounds it, and the bias can be referred to as a liquid gate bias $V_{lg}$. FIG. 2 is a diagram illustrating the estimated capture rate for 33-mer ssDNA, with a 300 mV bias applied, as a function of target concentration. Furthermore, the capture rate can be independent of the size of the target DNA being captured. Additionally or alternatively, and as described further below, the carrier density in the nanotube 110 can be controlled through a global back gate $V_{bg}$ applied through the substrate 115.

Nanotube and nanowire field-effect sensors can be utilized as biosensors. In some implementations, an electrolyte buffer with mobile ions can be used to gate the transistor. The sensing mechanism can be attributed at least in part to changes in the Schottky barrier at the contacts and electrostatic doping of the nanotube channel due to adsorption of biomolecules.

As embodied herein, introducing a defect onto the nanotube 110 surface can provide smFET 100 sensors with localized charge sensitivity and improved gain. Such defects can, in turn, be used to covalently bind molecules at the scattering site. The resulting smFET 100 device can have improved sensitivity and detect the binding of a single molecule, due at least in part to Coulomb interactions between the molecule and the defect which modulates scattering in the 1D channel. The charge sensitivity can be screened by counterions and can be localized to the region of the defect. The single-point defects can be electrochemically created in a controllable manner, as described in further herein. Such defect-dominated conductance in nanotubes can produce measurements of DNA hybridization kinetics with suitable high signal-to-noise ratio (SNR) and bandwidth to measure single-molecule kinetics and thermodynamics through a label-free smFET approach.

The point-functionalized defect areas on the smFETs 100, for example and as embodied herein, can be less than two nanometers in diameter. Scanning gate microscopy can be used to image the sensitivity of the nanotube 110 before and after the oxidation by using a biased tip (−5V) of an atomic force microscope. Before oxidation, electron transport in the nanotube can be sensitive both to the Schottky barrier of the lower electrode, and also to other points along the channel. After oxidation, the sensitivity can be localized to a region proximate the middle of the channel. A short chemical reaction with a strong oxidizer (for example potassium permanganate or the like) can convert the defect functional group to a carboxylic acid, to which a probe molecule can be covalently attached.

FIGS. 3A-3D are diagrams illustrating carbon nanotube FET time-domain measurements showing the two-level response to single-molecule hybridizations. As shown in FIG. 3B, capture probe 160, which can be terminated with an amine group and a three-carbon linker at the 5' end, can be covalently attached to the carboxyl defect 140 on the nanotube 100 through a standard coupling reaction using sulfo-N-hydroxysuccinimide (sulfo-NHS) and 1-ethyl-3-(3-dimethylaminopropyl) carbodiimide (EDC). As shown in FIG. 3A, the carbon nanotube 100, which was measured in 1×PBS buffer solution with a 10-mer oligonucleotide probe attached at the 5' end (NH2-5'-GTGAGTTGTT-3') (SEQ ID NO: 1), has a conductance with a single state dominated by flicker noise. In FIG. 3D, complementary ssDNA molecules were added to the solution, and the conductance exhibited two level fluctuations, as shown in FIG. 3C. Examining the fluctuations as a function of temperature can illustrate the high state in the conductance correlated to the defect with probe only and the low state correlated to a defect with duplex DNA. The negatively charged target DNA can modulate a tunnel barrier at the defect site through electrostatic interaction or scattering and can thereby reduce its conductance. Further details of exemplary single-molecule detection using nanotubes are shown and described in International Application No. PCT/US2012/020955, filed on Jan. 11, 2012, which is incorporated by reference herein in its entirety.

The effect of Debye length screening of the region around the point defect of the nanotube can be useful for the assay applications of the smFET 100 devices. In one example, measurements were performed with a 10-mer probe, covalently attached at the 5' end to the nanotube, and hybridized to targets of varying length such that the distance was varied between the 3' end of the target and the nanotube. As such, the probe lengths were comparable to the persistence length of ssDNA. FIGS. 4A-4D illustrate the results of the measurements. FIGS. 4A-4C are histograms illustrating the two-level conductance fluctuations that show binding and melting of targets of different length at a temperature of 17° C., which can be lower than the melting temperature. The resistance amplitude that resulted from these different target lengths is shown in FIG. 4D as a function of distance of the 3'-end of the target to the nanotube for a fixed buffer (embodied herein as 1×PBS). The results can be represented by simple Debye length screening $$\propto e^{\frac{x}{\lambda_d}},$$

where $\lambda_d$ represents the Debye length. Similar Debye-length trends can be shown by varying the buffer concentration. As such, the interactions of the biomolecular system can be controlled with the charge-sensitive region of the smFET 100 device through proximity and buffer strength.

Figure 5:
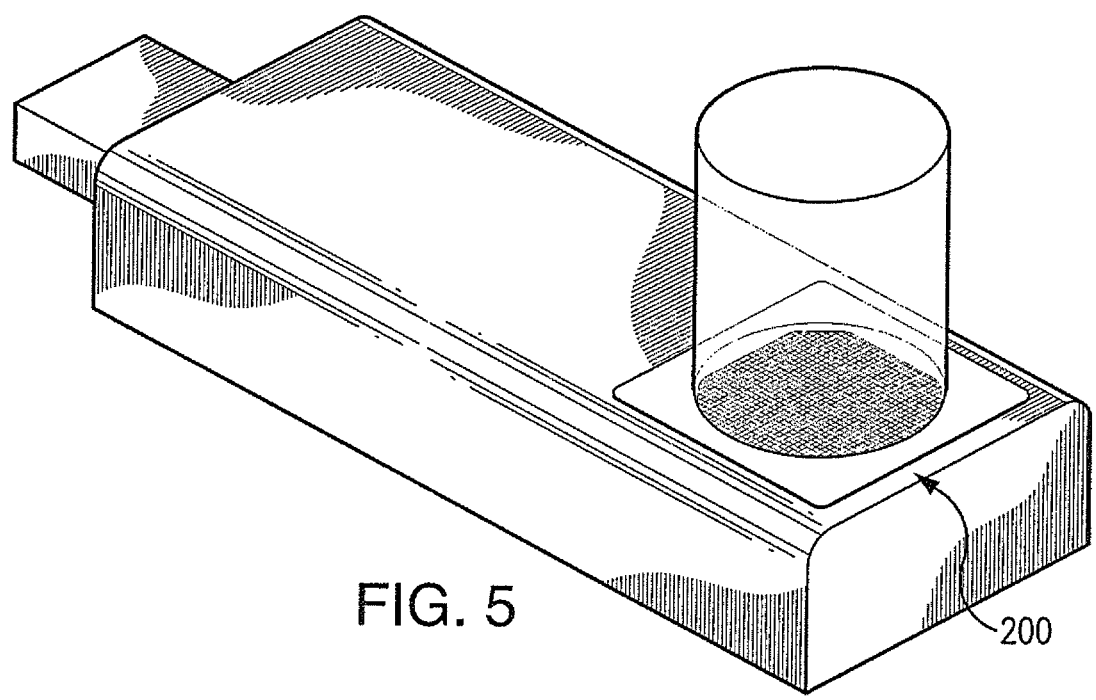
FIG. 5 is a diagram illustrating the assay platform of FIG. 1 configured on a form factor of a USB memory stick.
Figure 7:
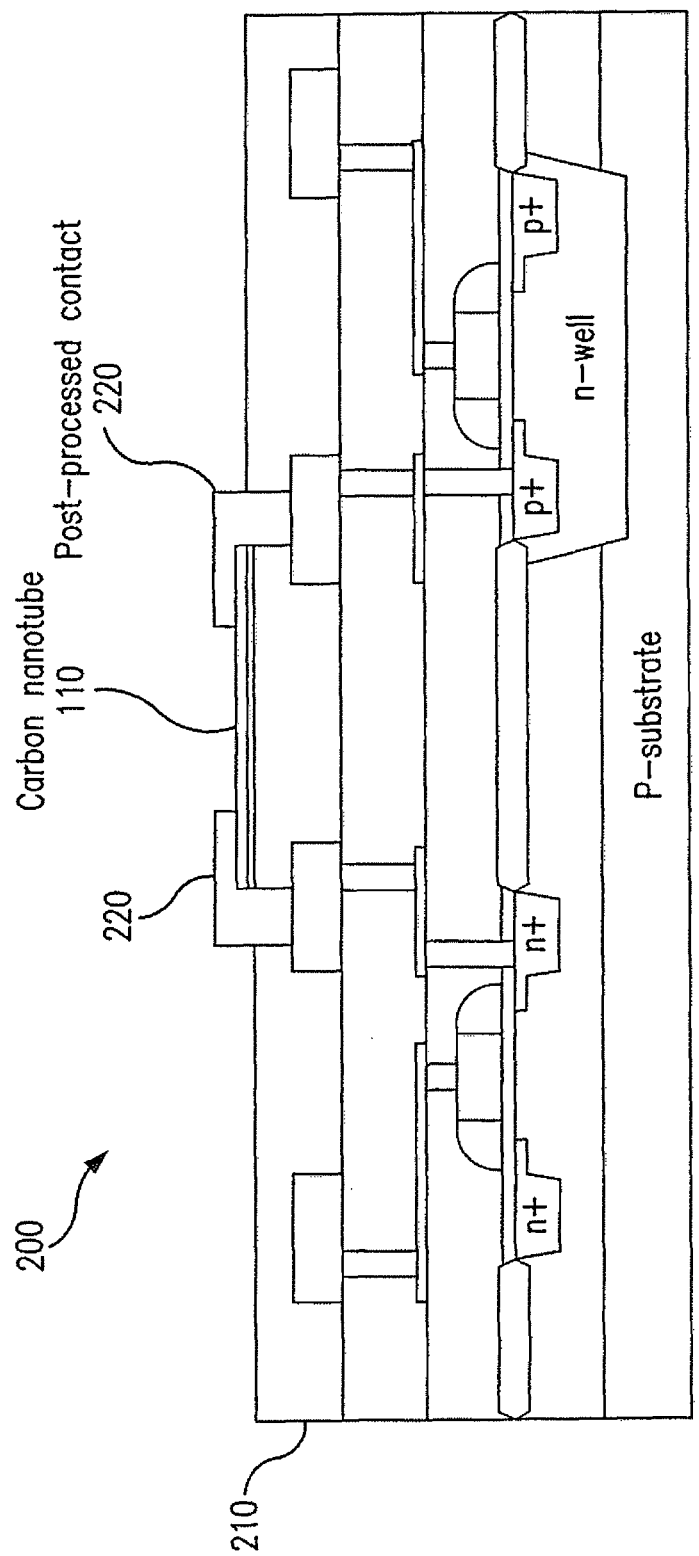
FIG. 7 is a diagram illustrating an exemplary embodiment of an integrated circuit and nanotube for a single-molecule nucleic-acid assay platform.

According to another aspect of the disclosed subject matter, an integrated circuit for a single-molecule nucleic-acid assay platform is provided. With reference to FIGS. 5-7, in an exemplary embodiment, the assay platform 200 can include one or more of smFETs 100 disposed on a complementary metal-oxide semiconductor (CMOS) integrated circuit 210. Platform 200 can allow for the development of an assay device 100 configured on a form factor of a USB memory stick, as shown for example in FIG. 5. The integrated circuit 210 can be configured, for example and without limitation, with dimensions from 1-mm to 10-mm on each side, and as embodied herein as a 5-mm-by-5-mm integrated circuit chip fabricated in an IBM 0.13-µm CMOS technology. Integrated circuit 210 can include, for example and without limitation, 10 to 100 measurement channels each multiplexed to 100 to 1000 smFET devices per channel, and as embodied herein having 12 measurement channels each multiplexed to 500 smFET devices per channel. Platform 200, in addition to improved integration, can allow for improved fabrication of these nanotube devices.

Various techniques can be utilized to transfer one or more nanotubes 110 to a substrate of a CMOS integrated circuit 210. FIG. 6A illustrates an exemplary technique for transferring nanotubes 110 to a substrate of CMOS integrated circuit 210. The technique of FIG. 6A involves spinning on the carbon nanotubes from a suspension. Alternatively, as illustrated in FIG. 6B, nanotubes 110 can be transferred by growing carbon nanotubes 110 on solid substrates and then spin on a polymer 205 (for example, embodied herein as polymethyl methacrylate) that can lift off in strong bases (for example, potassium hydroxide or sodium hydroxide) along with the nanotube 110. The thin film polymer 205 can then be placed on top of the CMOS substrate 210, along with the nanotubes 110. As such, the density of nanotubes 110 can be adjusted through the growth recipe. Furthermore, using quartz substrates can improve density and alignment of the nanotube 110 arrays, which can be suitable for biosensors. FIG. 6C illustrates another exemplary technique for transferring nanotubes 110 using dielectrophoresis. In this technique, by applying an AC voltage between electrodes 215a, 215b, a force can be applied to nanotubes 110 proportional to the gradient of electric fields. The CMOS chip 210 can aid in applying the field and stop the field when a nanotube 110 has bridged the electrodes. In each of the above transfer techniques, an active CMOS chip 210 with a dense electrode array, for example having 550 or more electrode pairs per mm$^2$, can be used to locate where a nanotube bridges two contacts, and in this manner can guide the location of the nanotubes 110.

After transfer of nanotubes 110 to the substrate of the CMOS integrated circuit 210, additional lithography and metallization can be performed to deposit a metal, such as titanium, to form electrodes 220a, 220b connecting the nanotubes 110 to the integrated circuit 210, as shown for example in FIG. 7. The metal can be deposited onto exposed aluminum electrodes on substrate 215, or alternatively, the exposed aluminum electrodes can be etched away and replaced with titanium. Additionally, a further set of surface-exposed aluminum electrodes can be etched away and replaced with gold. The gold electrodes can be used to create one or more integrated reference electrodes 225 to allow control of the electrolytic potential gating the nanotube sensors. Integrated circuit 210 can be wirebonded to a ball-grid array (BGA) package. A dam-and-fill doughnut epoxy encapsulation (for example, using Hysol FP4451 dam and FP4650 fill) can cover the exposed gold wirebonds, which can leave the die surface exposed. The reference electrodes 225 can be formed, for example and without limitation, by electroplating silver with subsequent chlorination with FeCl3. The reference electrodes can thus be configured as Ag/AgCl electrodes, which can have a relatively low current level therethrough, and thus can operate for days continuously before being exhausted. Chlorination of the Ag/AgCl electrodes can be repeated multiple times before the silver electrode can become exhausted and can need to be re-electroplated. Additionally or alternatively, platinum can be deposited to create the reference electrodes 225 to allow control of the electrolytic potential gating the nanotube 110. Platinum can be deposited onto the set of surface-exposed aluminum electrodes, or the set of surface-exposed aluminum electrodes can be etched away and replaced with platinum. Additionally or alternatively, one or more external reference electrodes 125 can be utilized to allow control of the electrolytic gating potential, as described herein.

Integration of nanotubes 110 with CMOS chips 210 can allow multiple devices to be integrated on the same measurement substrate and can allow reduction in the parasitic capacitance associated with assay measurements. As such, measurement bandwidth can be increased while reducing amplifier noise. Furthermore, the integrated circuit 210 CMOS substrates can also be automated to quickly probe devices and select those with suitable performance.

Concentrations of target analytes can be determined by the mean time between capture events, as shown for example in FIG. 2. Concentrations as low as 100 fM can be detectable within approximately 8 hours. The assays can be performed at a temperature such that after capture, there is suitable thermal energy, which can be based at least in part on the size of the target and the buffer concentration, for the captured molecule to escape again and allow for a new capture event. After a capture event, the molecule can again be recaptured. The detailed kinetics of these multiple capture events can provide additional information to identify single-nucleotide polymorphisms (SNPs) and other partial mismatches. By contrast, in certain microarrays, concentration and mismatch affinity can not be independently determined.

Capture probe 160 can be immobilized or programmed on a site-specific basis, for example and as embodied herein through either robotic spotting or through electrically programmed immobilization. With robotic spotting, drops of capture probe 160 can be placed over each selected site. In this manner, sensor density can have a pitch as low as approximately 150-μm. With electrically programmed immobilization, individual probe sites can be electrically selected such that only those selected sites can bind the probe. In this manner, sensor density can be increased without limit over that obtained with robotic spotting.

Example

Figure 8A:
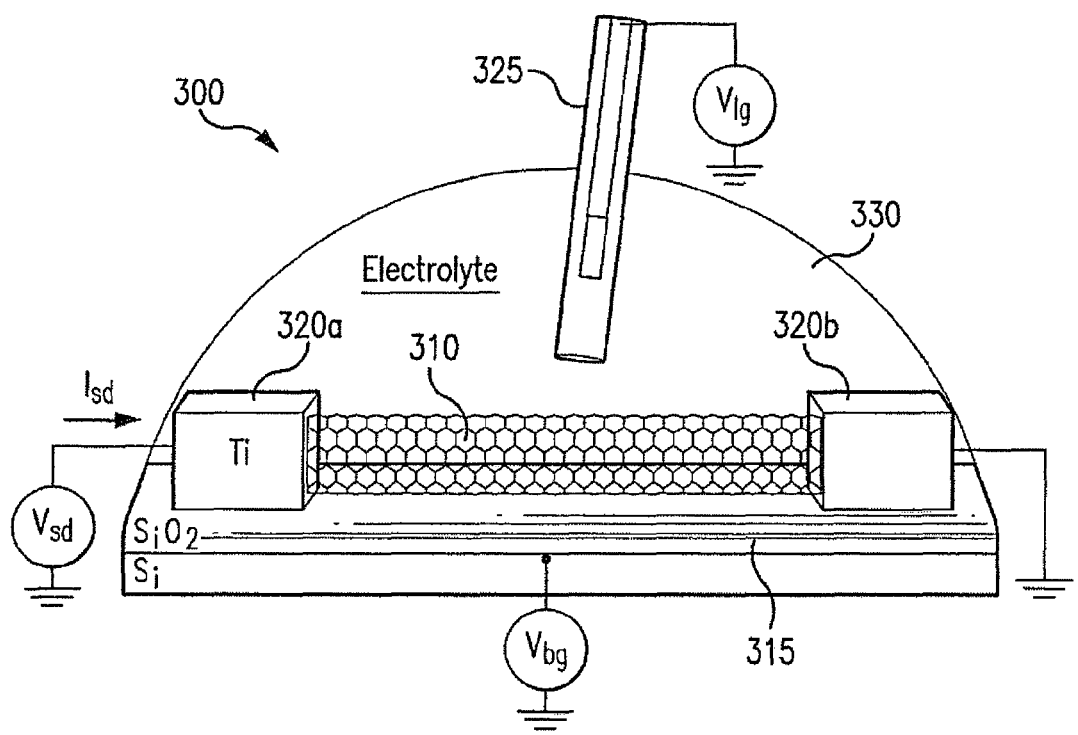
FIGS. 8A-8C are diagrams illustrating an exemplary assay platform according to the disclosed subject matter.
Figure 8B:
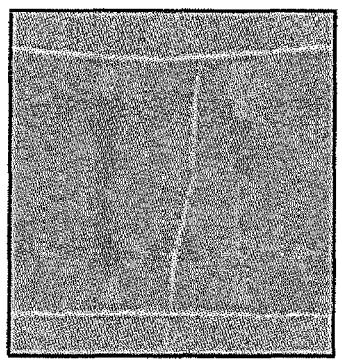

In one example, chemical vapor deposition was used to grow carbon nanotubes 310 approximately 1.4-1.6 nm in diameter on silicon wafers 315 with a thin (about 300 nm) grown silicon oxide layer. Photolithography was used to pattern titanium electrodes on top of the grown nanotubes to make source and drain contacts separated by about 2.5 μm. From a single carbon nanotube 310, 20-30 individual devices can be created, which can then be wirebonded and epoxy encapsulated to perform the following biological assay techniques. An exemplary smFET assay platform 300 configuration is shown in FIG. 8A, for purpose of illustration. A small bias can be applied between the source and drain electrodes 320a, 320b, embodied herein as titanium electrodes, on the order of 100 mV, and a current can be measured through the individual carbon nanotube 310, as shown for example in the scanning electron microscope image of FIG. 8B.

Figure 8C:
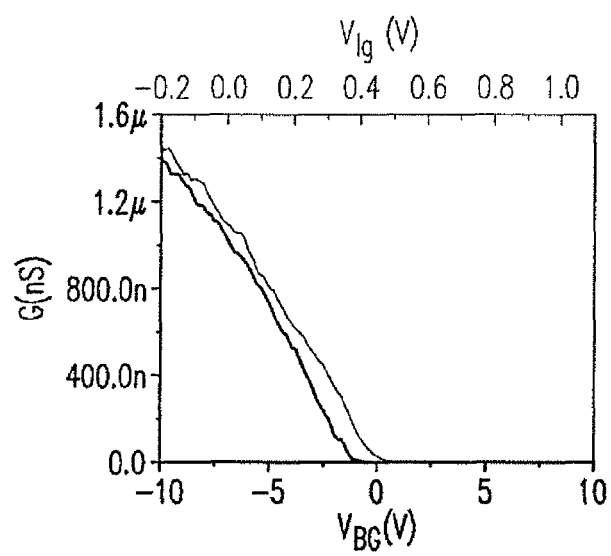

The carrier density in the nanotube 310 can be controlled through a global back gate $V_{bg}$. The carbon nanotube 310 can also be gated through the liquid electrolyte 330, for example by controlling the electrolyte potential with an Ag/AgCl or platinum pseudo reference electrode 325. Mobile ions in the electrolyte 330 can cause an electric field at the nanotube liquid interface and induce carriers in the nanotube channel. The amount by which the potential drops can be given by the Debye length, as described further herein, which, as embodied herein, can be about 0.7 nm for a liquid electrolyte 340 buffer of 1×PBS at a pH of 7.4. Due at least in part to the larger capacitance ($C_{lg}/C_{BG} \sim 10$), the semiconducting nanotube 310 can be turned off at smaller voltages with the electrolyte gate $V_{lg}$ than with the back gate $V_{bg}$, as shown for example in FIG. 8C, which illustrates the current through the back gate (bottom) and liquid gate (top).

Figure 9B:
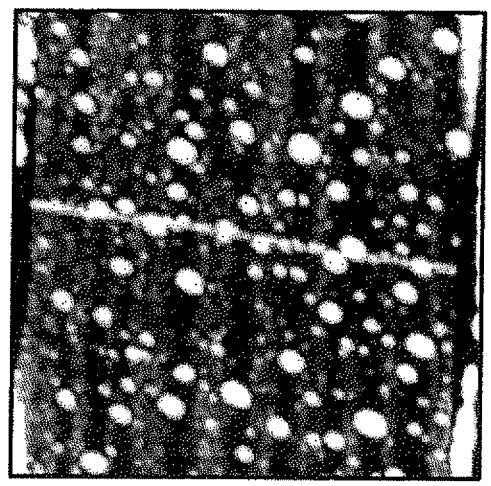
FIGS. 9A-9D are diagrams illustrating further details of the assay platform of FIG. 8A.
Figure 9A:
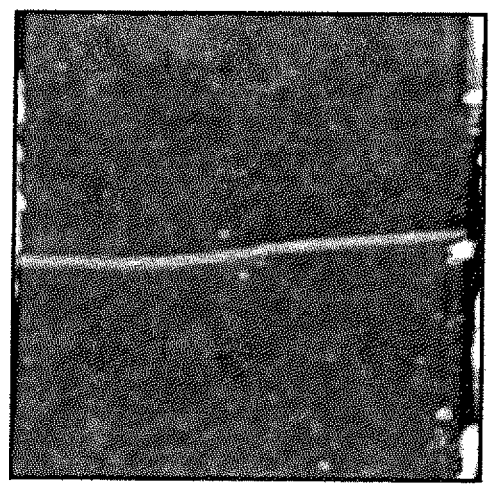
Figures 9C, 9D:
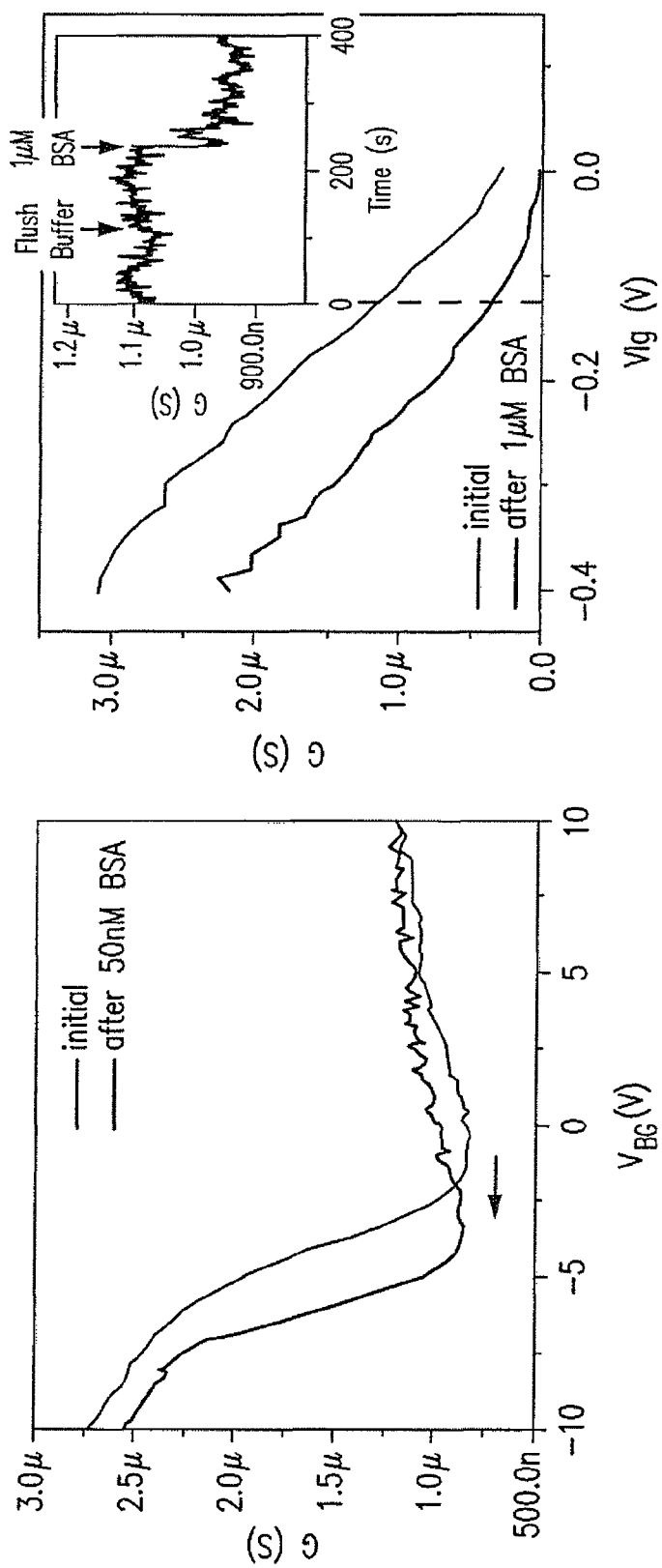

One-dimensional conductors, such as single-walled carbon nanotubes, can act as high-gain field-effect sensors, in which the conductance can vary strongly with local charge density. As an example of ensemble sensing using the assay platform 300 to sense bovine serum albumin (BSA) is provided. FIG. 9A is an atomic force microscope (AFM) image showing carbon nanotube 310 of assay platform 300. The nanotube 310 was immersed in 50 nM BSA in 1×PBS solution for 1 hour, which is shown in the AFM image of FIG. 9B. As shown in FIG. 9B, the BSA proteins tend to stick preferentially to the carbon nanotube 310. The device 300 was measured before and after this exposure using the back gate in air and the adsorbed protein cause a doping of the channel, resulting in a threshold shift of −3V, as shown in FIG. 9C. A shift in the same direction was also observed in device 300 under the aqueous buffer. For purpose of comparison, as shown in FIG. 9D, the Ag/AgCl electrolyte gate $V_{lg}$ response was shifted by around −120 mV when exposed to a 1 μM BSA buffer, which is also illustrated in real time in the inset of FIG. 9D. In this manner, the device 300 was held under a constant bias and the conductance was observed. The device 300 shows no response when only the electrolyte solution is applied, but a drop in conductance is measured when the device 300 is immersed in the BSA solution. As such, carbon nanotube 310 in assay device 300 can be used for label-free detection of biomolecules.

Sensitivity of device 300 can be improved by creating a point defect 340 in the carbon nanotube 310, which can reduce the region of charge sensitivity to the region around the defect. The defect can be created, as embodied herein, by conductance-controlled electrochemical etching of the tube in 1 M sulfuric acid using a platinum electrode, followed by a 30 to 45 s exposure to 6.5 mM potassium permanganate to create a defect with a carboxylic acid functional group.

Figure 10:
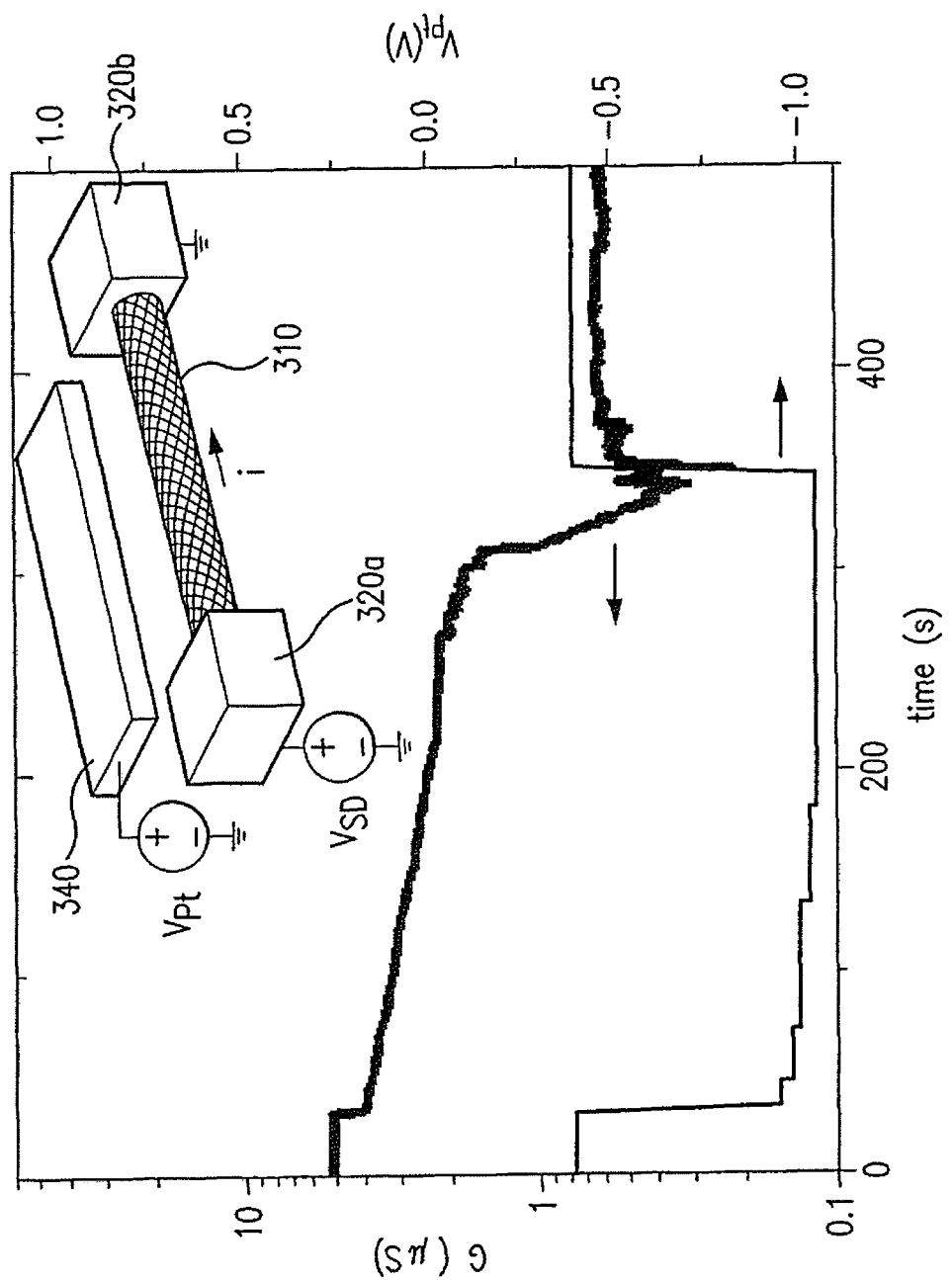
FIG. 10 is a diagram illustrating further details of the assay platform of FIG. 8A.

Conductance-based oxidation of the carbon nanotube 310 is illustrated in FIG. 10. As shown in FIG. 10, as the electrolytic gate voltage applied to the platinum electrode was changed below a threshold voltage (around −1V), the conductance exhibits a slow decrease, followed by an abrupt jump. A Labview program detected this jump and immediately ramped up the platinum voltage in order to avoid further oxidation. The potential was held constant, and the device was immersed in 6.5 mM potassium permanganate to create the carboxylic acid functional group.

Scanning gate microscopy (SGM), which used the biased tip of an atomic force microscope as a localized gate, was used to characterize the location of the defect 340. FIG. 11A shows an SGM image of the defect overlaid with a topography image of nanotube 310. The Schottky barriers at the contacts (shown in FIG. 11A as the darker areas) can be seen when the tip is biased with a −5 V bias. With the presence of point defect 340, the sensitivity can be localized to a small region around the center of the nanotube, as shown in FIG. 11B. Localization can be further illustrated by a coupling reaction with gold-labeled streptavidin. A gold nanoparticle can be found around the region of highest sensitivity, as shown in FIG. 11C, indicating that the defect can be both localized and chemically reactive.

In one example, device 300 can be used to measure DNA hybridization. A 10-mer DNA probe with an amine group at the 5' end (NH2-5'-GTGAGTTGTT-3') (SEQ ID NO: 1) was attached to the point defect 340 in the 310 nanotube by an amine to carboxylic acid coupling reaction assisted by 1-ethyl-3-(3-dimethylaminopropyl) carbodiimide (EDC) and sulpho-N-hydroxysuccinimide (sulpho-NHS). The device 300 was rinsed with deionized water, and the conductance was monitored in phosphate buffered saline buffer (1×PBS). FIG. 12A illustrates real time conductance data obtained with the DNA probe 360 only, with a corresponding histogram of the data illustrated in FIG. 12B. As shown in FIG. 12A, no particular features in the conductance are observed and the device 300 exhibits flicker (1/f) noise. The histogram of the conductance shows the conductance data fit to a single Gaussian pattern, as shown in FIG. 12B.

The device 300 was then exposed to a 1 μM complementary DNA concentration 350 at 28° C. FIG. 12C illustrates real time conductance data obtained with the complementary DNA concentration 350 added, with a corresponding histogram of the data illustrated in FIG. 12D. As shown in FIG. 12C, the device 300 exhibits two-level fluctuations, which can also be seen in the corresponding histogram in FIG. 12D. In this manner, a model can be shown in which the low-conductance state represents device 300 with DNA in the duplex form and the high-conductance state with only DNA probe 360 attached.

Figure 13A:
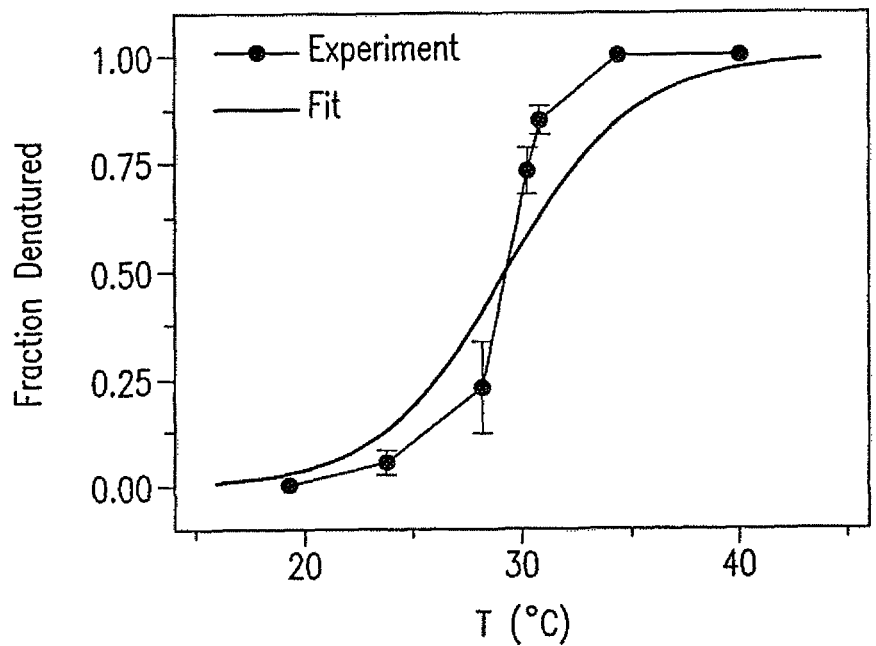
FIGS. 13A-13B are diagrams illustrating further details of the assay platform of FIG. 8A.
Figure 13B:
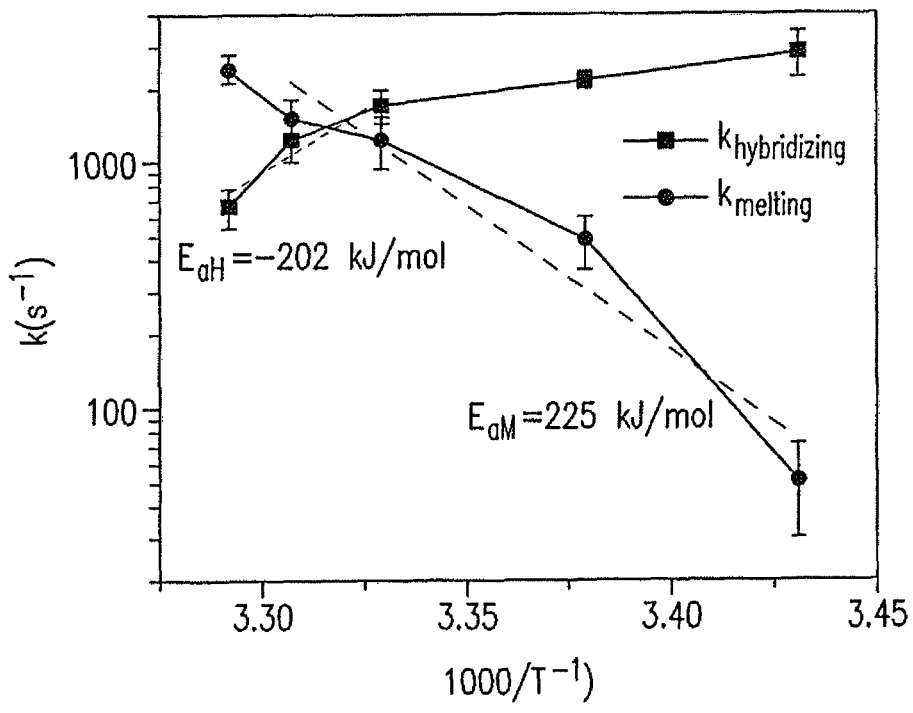

In addition to the two-level fluctuations, there was a small decrease in the overall conductance level with the addition of target DNA 350, which can be attributed at least in part to non-specific adsorption to the sidewall of the nanotube 310. From the model, a DNA melting curve (shown in FIG. 13A) can be extracted by taking the ratio of the areas under the Gaussian fits to the histograms in FIG. 12D. The melting point measured with the nanotube conductance on a single DNA molecule was slightly lower (29.4° C.) than the measurements in solution by UV-Vis spectroscopy (36.2° C.). The fit can be represented by the Langmuir isotherm K=a/(1−a)C, where C can represent the concentration of target DNA together with the thermodynamic relationship −RT ln(K)=ΔH°−TΔS°. The kinetics of both the high and low states were also determined, as shown in the Arrhenius plot in FIG. 13B.

Figure 14B:
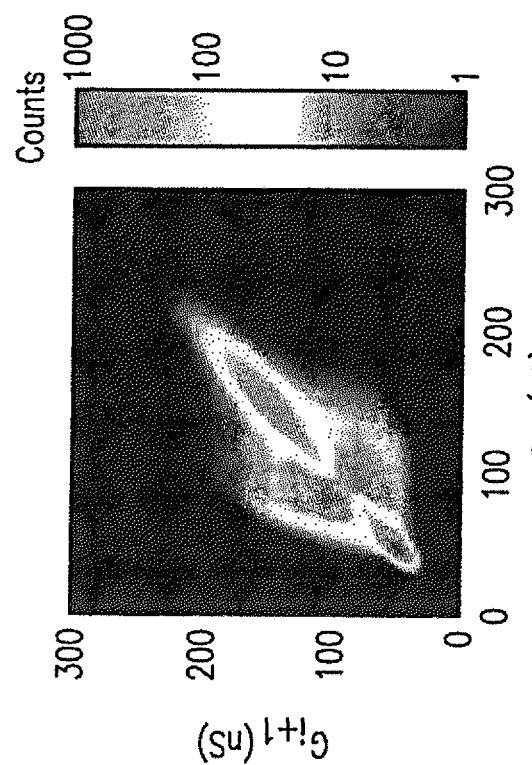
FIGS. 14A-14B are diagrams illustrating further details of the assay platform of FIG. 8A.
Figure 14A:
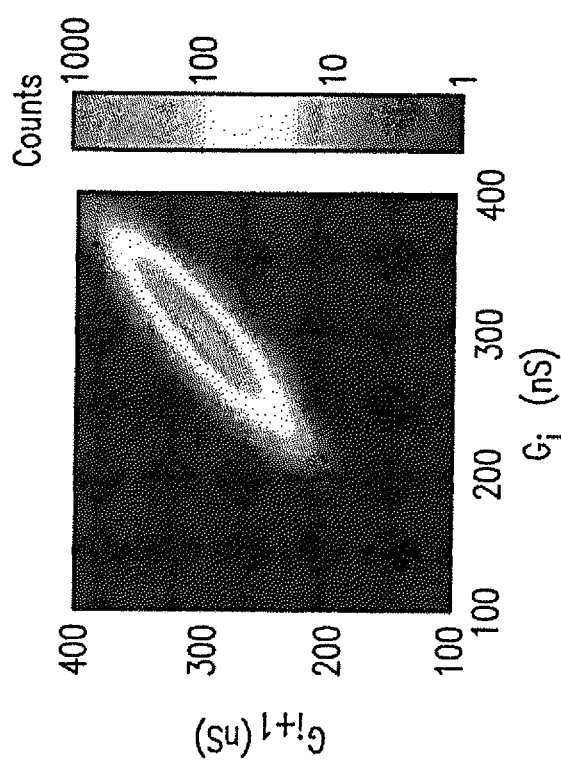

Random telegraph noise can be a challenge in nanoscale CMOS devices. The assay devices according to the disclosed subject matter, which can be sealed to nanometer dimensions, can be affected by trapping phenomena at the silicon-dielectric interface in one or more traps. Certain data analysis techniques, including time lag plots (TLP), which are two dimensional histograms of the conductance at consecutive data points, can be utilized to analyze random telegraph noise. FIG. 14A is a diagram illustrating the single state in the TLP with DNA probe 360 only. FIG. 14B illustrates the two-states in the TLP after adding complementary DNA target 350.

Figure 15B:
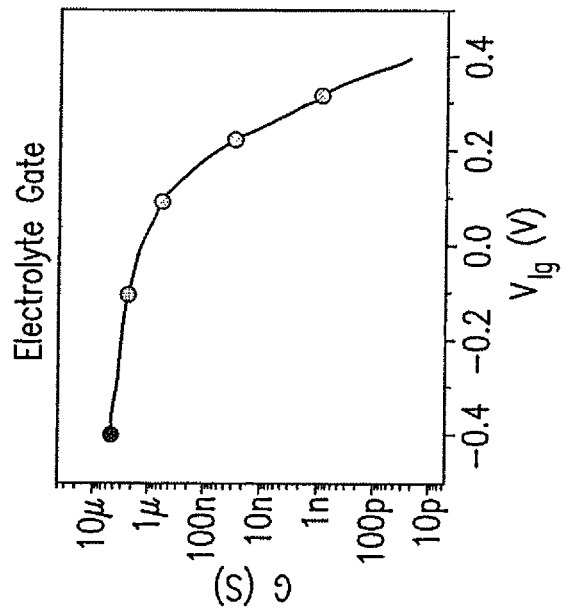
Figure 15A:
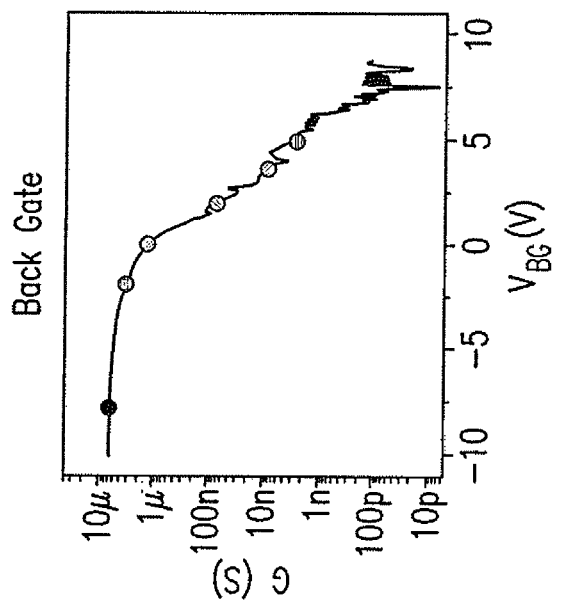

Having the channel of device 300 exposed to the environment can be advantageous at least in part because molecules can be directly tethered to it, which can improve sensitivity of the device 300. However, small fluctuating changes in the environment can affect the electronic transport. The underlying noise of device 300 can be examined. FIGS. 15A-15B illustrate the noise power spectral density of the carbon nanotube 310 current as a function of bias both for the back gate configuration (FIG. 15A) and the electrolyte gate (FIG. 15B). FIGS. 15C-15D illustrate the corresponding flicker noise for the back gate configuration (FIG. 15C) and the electrolyte gate (FIG. 15D). FIGS. 15A-15D illustrate that, for each configuration, the noise included mostly flicker or 1/f noise, and the noise amplitude was similar.

Figure 16:
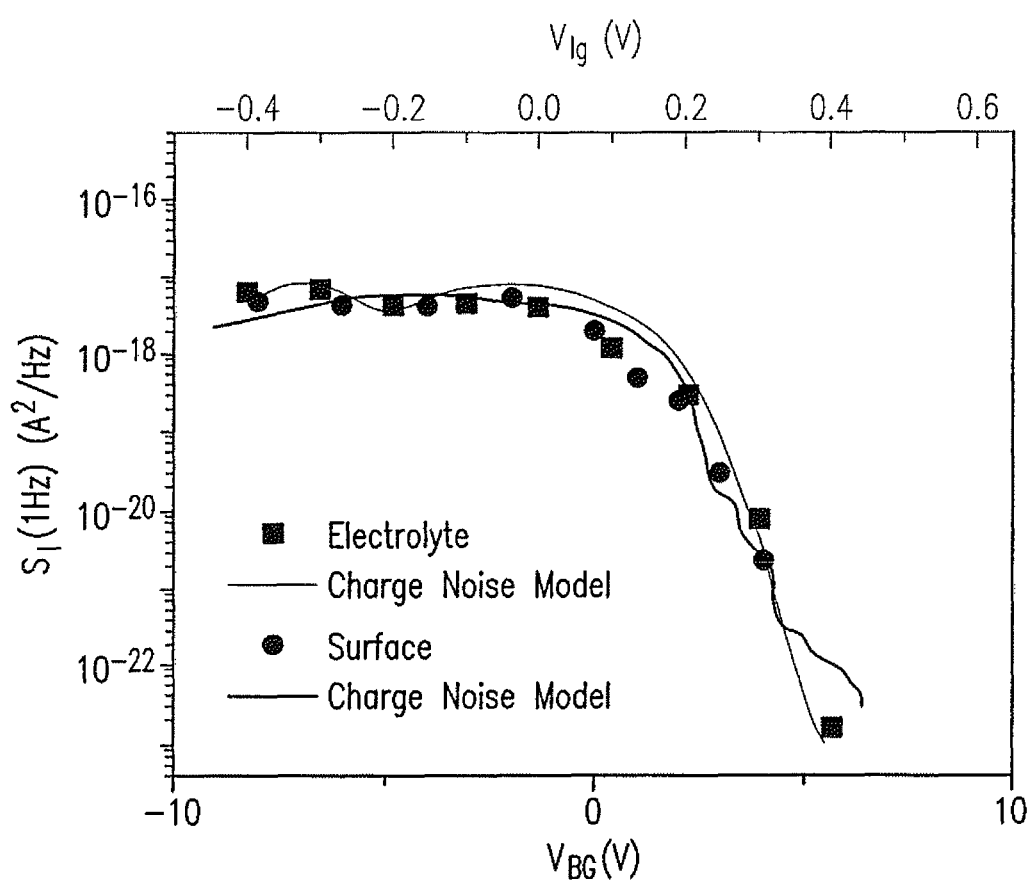
FIG. 16 is a diagram illustrating further details of the assay platform of FIG. 8A.

Two exemplary models can be utilized to represent the flicker noise in carbon nanotube 310. The first exemplary model can be the empirical Hooge model, which can suggest that noise can be caused by independent scattering events of charge carriers, and as such can scale inversely with the number of charge carriers in the nanotube 310. The second exemplary model can be the charge-noise model, which can suggest that noise can be attributed to random fluctuations of charge in the environment of the channel. The flicker noise can be represented by the charge-noise model as:

$$S_I \propto 1/C_g^2 (dI/dV_g)^2, \tag{1}$$

where S can represent the noise due to fluctuations of local environmental charge, $C_g$ can represent the capacitive coupling between the gate and the carbon nanotube 310, dI can represent the change in current through the nanotube 310 and $dV_g$ can represent the change in gating potential of the nanotube 310. As shown in FIG. 16, the noise spectrum and fitted to the above charge-noise model using the gate sweeps in FIGS. 15A-15B. One difference between the back gate and the liquid gate can be the gate capacitance. As such, the liquid itself can be considered to not contribute significant noise, which can be beneficial for biosensor applications in aqueous environments. The majority of the noise can be due at least in part to both traps at the interface between the nanotube 310 device and the dielectric substrate on which the nanotube 310 device is supported and noise from diffusion or absorption/desorption of biomolecules near the point defect 340.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

The invention claimed is:

1. An integrated circuit for a single-molecule nucleic-acid assay platform, comprising:
   a CMOS substrate;
   an array of single-molecule field-effect transistors (smFETs) disposed on a surface of the CMOS substrate, each smFET comprising one or more carbon nanotubes and a capture probe coupled thereto, the capture probe configured to transmit hybridization information including time information between a first captured single target nucleic acid molecule proximate thereto and a second captured single target nucleic acid molecule proximate thereto; and
   at least one pair of electrodes disposed proximate opposing ends of the one or more carbon nanotubes to electrically couple the one or more carbon nanotubes to the CMOS substrate, wherein the one or more carbon nanotubes and the at least one pair of electrodes are surrounded by an electrolyte buffer.

2. The integrated circuit of claim 1, wherein the CMOS substrate comprises a substrate having dimensions of no more than 5 mm by 5 mm.

3. The integrated circuit of claim 1, wherein the array comprises at least 12 measurement channels.

4. The integrated circuit of claim 3, wherein each of the measurement channels is multiplexed to at least 500 smFETs.

5. The integrated circuit of claim 1, wherein the one or more carbon nanotubes comprises a point defect formed on a portion thereof.

6. The integrated circuit of claim 5, wherein the point defect is configured to transmit the hybridization information for the single target nucleic acid molecule.

7. The integrated circuit of claim 2, wherein the at least one pair of electrodes comprises titanium.

8. The integrated circuit of claim 2, further comprising one or more reference electrodes on the substrate to allow control of an electrolytic gating potential.

9. The integrated circuit of 8, wherein the one or more reference electrodes comprises one or more Ag/AgCl electrodes or platinum electrodes.

10. The integrated circuit of claim 2, further comprising a ball-grid array (BGA) package coupled to the at least one pair of electrodes.

11. The integrated circuit of claim 2, further comprising a processor coupled to the array and configured to determine a capture rate from the hybridization information.

12. The integrated circuit of claim 1, wherein the array of single-molecule field-effect transistors (smFETs) is disposed on a top surface of the substrate and defines an exterior surface of the integrated circuit.

* * * * *